US011591640B2

(12) United States Patent
Cunningham et al.

(10) Patent No.: US 11,591,640 B2
(45) Date of Patent: Feb. 28, 2023

(54) PHOTONIC RESONATOR ABSORPTION MICROSCOPY (PRAM) FOR DIGITAL RESOLUTION BIOMOLECULAR DIAGNOSTICS

(71) Applicant: The Board of Trustees of the University of Illinois, Urbana, IL (US)

(72) Inventors: Brian T. Cunningham, Champaign, IL (US); Yue Zhuo, Champaign, IL (US); Brendan Harley, Urbana, IL (US); Ji Sun Choi, Urbana, IL (US); Thibault Marin, Champaign, IL (US); Yi Lu, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 52 days.

(21) Appl. No.: 17/328,752

(22) Filed: May 24, 2021

(65) Prior Publication Data

US 2021/0324456 A1 Oct. 21, 2021

Related U.S. Application Data

(62) Division of application No. 16/170,111, filed on Oct. 25, 2018, now Pat. No. 11,041,187.
(Continued)

(51) Int. Cl.
*C12Q 1/6825* (2018.01)
*G01N 21/552* (2014.01)
(Continued)

(52) U.S. Cl.
CPC ......... *C12Q 1/6825* (2013.01); *C12Q 1/6886* (2013.01); *G01N 21/554* (2013.01); *G01N 21/774* (2013.01); *C12Q 2600/178* (2013.01)

(58) Field of Classification Search
CPC ............ C12Q 2600/178; C12Q 1/6825; C12Q 1/6886; C12Q 2523/313; C12Q 2563/155;
(Continued)

(56) References Cited

U.S. PATENT DOCUMENTS 7,023,544 B2 4/2006 Cunningham et al.
7,264,973 B2 9/2007 Lin et al.
(Continued)

FOREIGN PATENT DOCUMENTS

CN 102719526 A 10/2012

OTHER PUBLICATIONS

Peterson et al., Biosensors and Bioelectronics, vol. 74, Jul. 23, 2015, pp. 815-822.
(Continued)

*Primary Examiner* — Maureen Wallenhorst
(74) *Attorney, Agent, or Firm* — McDonnell Boehnen Hulbert & Berghoff LLP

(57) ABSTRACT

A digital assay for a micro RNA (miRNA) or other target analyte in a sample makes use of nanoparticles that absorb light at the resonant wavelength of a photonic crystal (PC). Such nanoparticles locally quench the resonant reflection of light from the PC when present on the surface of the PC. The nanoparticles are functionalized to specifically bind to the target analyte, and the PC surface is functionalized to specifically bind to the nanoparticles that have bound to the target analyte. The sample is exposed to the functionalized nanoparticles, and the individual nanoparticles bound to the PC surface can be identified and counted based on reduced intensity values in the reflected light from the PC. The number of bound nanoparticles that are counted in this way can be correlated to the abundance of the target analyte in the sample.

19 Claims, 5 Drawing Sheets

Related U.S. Application Data

(60) Provisional application No. 62/577,240, filed on Oct. 26, 2017.

(51) Int. Cl.
    *G01N 21/77* (2006.01)
    *C12Q 1/6886* (2018.01)

(58) Field of Classification Search
    CPC .... G01N 21/553; G01N 21/554; G01N 21/77; G01N 21/774; G02B 21/00; Y10T 436/2575
    USPC ... 436/523, 525, 526, 63, 94, 164, 165, 180; 422/82.05, 82.09, 502, 503
    See application file for complete search history.

(56) References Cited

U.S. PATENT DOCUMENTS

| | | |
|---|---|---|
| 7,292,336 B2 | 11/2007 | Cunningham et al. |
| 7,298,477 B1 | 11/2007 | Cunningham et al. |
| 7,479,404 B2 | 1/2009 | Cunningham et al. |
| 7,521,769 B2 | 4/2009 | Cunningham |
| 7,531,786 B2 | 5/2009 | Cunningham et al. |
| 7,737,392 B2 | 6/2010 | Cunningham et al. |
| 7,742,662 B2 | 6/2010 | Cunningham |
| 7,968,836 B2 | 6/2011 | Cunningham et al. |
| 8,298,780 B2 | 10/2012 | Wagner et al. |
| 9,400,353 B2 | 7/2016 | Cunningham et al. |
| 9,921,165 B2 | 3/2018 | Bailey et al. |
| 11,041,187 B2 | 6/2021 | Cunningham et al. |
| 2009/0079976 A1 | 3/2009 | Cunningham et al. |
| 2013/0065777 A1 | 3/2013 | Altug et al. |
| 2017/0205405 A1 | 7/2017 | Tamayo De Miguel et al. |
| 2017/0327888 A1 | 11/2017 | Ong et al. |
| 2018/0179588 A1 | 6/2018 | Zhang et al. |
| 2019/0120766 A1 | 4/2019 | Cunningham et al. |

OTHER PUBLICATIONS

Peterson et al., Sensors, vol. 17, 2203, 2017, pp. 1-13.
Canady et al., PNAS, vol. 116, No. 39, Sep. 9, 2019, pp. 19362-19367.
S.X. Chen et al., "An Engineered Kinetic Amplification Mechanism for Single Nucleotide Variant Discrimination by DNA Hybridization Probes," J Am. Chem. Soc. 138, 5076-5086 (Mar. 24, 2016).
N. Gandra et al., "Plasmonic Planet-Satellite Analogues: Hierarchical Self-Assembly of Gold Nanostructures," Nano Letters 12, 2645-2651 (Apr. 25, 2012).
L.M. Tian et al., "Gold Nanorods as Plasmonic Nanotransducers: Distance-Dependent Refractive Index Sensitivity," Langmuir 28, 17435-17442 (Nov. 19, 2012).
A. Abbas et al., "Hot Spot-Localized Artificial Antibodies for Label-Free Plasmonic Biosensing," Adv. Funct. Mater. 23 (14): 1789-1797 (Apr. 12, 2013).
L. Gu et al., "MicroRNAs as prognostic molecular signatures in renal cell carcinoma: a systematic review and meta-analysis," Oncotarget 6, 32545 (Oct. 20, 2015).
X. Huang et al., "Exosomal miR-1290 and miR-375 as prognostic markers in castration-resistant prostate cancer," Eur. Urol. 67(1): 33-41 (Jan. 2015).
J. Miao et al., "A plasmonic colorimetric strategy for visual miRNA detection based on hybridization chain reaction," Sci Rep. 18, 32219 (Aug. 18, 2016).
L. Wu et al., "Continuously Tunable Nucleic Acid Hybridization Probes," Nat. Methods 12(12): 1191-1196 (Dec. 2015).
Y. Zhuo et al., "Single nanoparticle detection using photonic crystal enhanced microscopy," Analyst 139, 1007 (Jan. 8, 2014).
Y. Zhuo et al., "Label-Free Biosensor Imaging on Photonic Crystal Surfaces," Sensors 15, 21613-21635 (Aug. 28, 2015).

PHOTONIC RESONATOR ABSORPTION MICROSCOPY (PRAM) FOR DIGITAL RESOLUTION BIOMOLECULAR DIAGNOSTICS

CROSS-REFERENCE TO RELATED APPLICATIONS

This application is a division of U.S. patent application Ser. No. 16/170,111, filed Oct. 25, 2018, now U.S. Pat. No. 11,041,187, which claims priority under 35 U.S.C. § 119(e) to U.S. Provisional Application No. 62/577,240, filed Oct. 26, 2017. The foregoing applications are incorporated herein by reference.

STATEMENT REGARDING FEDERALLY SPONSORED RESEARCH

This invention was made with government support under CBET 11-32301 awarded by the National Science Foundation and under RO1 DK099528 and R21 EB018481 awarded by the National Institutes of Health. The Government has certain rights in this invention.

BACKGROUND

Traditionally, drug development and cancer therapeutic selection has targeted patient and tumor histology characteristics for potential drug testing for efficacy. However over the last decade, a paradigm shift in this practice has taken place because of the tremendous progress achieved in detection instrumentation and molecular techniques allowing the identification of aberrant genes and/or pathways that drive tumor biology and patient response to treatments. This has led to the incorporation of molecular pathology-driven tumor profiling and diagnostics into clinical practice. Subtyping the genetic heterogeneity of tumors that is undecipherable with histology alone has provided knowledge of novel molecular targets that are currently being exploited for therapeutic gain, prognosis, and prediction of therapeutic responses to specific treatments.

Recent therapeutic advances in treating prostate cancer have resulted in significant improvements by enhancing the quality of life and longevity. Advanced metastatic prostate cancer is initially hormone sensitive, and is treated with androgen deprivation therapy (ADT) that controls progression, but which is not a cure. Patients inevitably progress with a median time period of 20 months to the metastatic castrate resistant prostate cancer (mCRPC) stage. Since 2010, the FDA has approved six novel treatments to control mCRPC, of which Abiraterone Acetate (AA) is one of the first drugs to use after ADT failure. It is a selective steroidal irreversible inhibitor of CYP17 (17 hydroxylase/C17,20-lyase) which blocks two important enzymatic activities in the synthesis of testosterone. This results in depleted androgen levels in the cancer tissue and clinically translates (in both pre- and post-docetaxel chemotherapy mCRPC stage) to durable control of cancer progression. In the pre-chemotherapy setting, 62% patients have a PSA decrease, with 30-40% patients having an objective response. Similarly the five other approved therapies in this stage have also demonstrated the ability to slow disease progression, but only for some patients for different durations of time. These advances, while rewarding, have led to the challenge of deciding how to choose from the therapeutic menu of options for treating individual patients, as there are no predictive factors for any of these treatments.

There is a major current interest in replacing this age-old clinical paradigm of approaches based upon clinical estimates with a gene-based treatment paradigm by harnessing the ability to identify aberrations in the cancer genome. The coupling of genomic markers with therapeutic advances is increasingly relevant as cancer medicines target stage-specific genetic abnormalities. The promise of "precision medicine" which seeks to match personalized medicine to personalized genomes may soon be realized due to the rapid advances in next-generation sequencing, which can rapidly decipher the mutational landscapes of cancers. It may be further possible to characterize of the genomic landscape of the primary tumor, in metastases, and in blood. Detection in blood, especially if a sample can be noninvasively gathered in the form of a droplet from a finger stick, represents a compelling advance for diagnostic technology, as it avoids performing invasive biopsies.

The term "liquid biopsy" describes the screening of genomic abnormalities attributable to circulating molecules that are shed by cancer cells in the blood of cancer patients from a blood draw or in a drop of blood. For example, in advanced prostate cancer, patients who have developed castrate resistance correlate with the presence of microRNAs (miRNA) miR-375 and miR-1290 in their plasma. See X. Huang et al., "Exosomal miR-1290 and miR-375 as Prognostic Markers in Castration-resistant Prostate Cancer," *European Urology*, pp. 33-41, 2015. These miRNAs are small (~22 nt) regulatory RNA molecules whose function is to modulate the activity of specific mRNA targets that play important roles in a wide range of pathologies, particularly in cancer. More generally, miRNAs are a powerful class of blood-based biomarkers for cancer detection because their expression is frequently dysregulated in cancer, their expression patterns are tissue specific, and they are stable in plasma or serum through encapsulation by exosomes. Due to the increased use of genome sequencing tools to identify new miRNA biomarkers and related efforts to validate them, specific miRNA sequences can be identified that are expressed by cancer cells at moderate or high levels, but are present at very low (or undetectable) levels in healthy individuals, and different types of tumors have distinct miRNA profiles. As a result, detection of miRNAs is now considered to be useful for early diagnosis, staging, and monitoring of cancer.

Reverse transcriptase quantitative PCR (RT-qPCR) and microarrays have been developed for detection of miRNAs. However, because the short length of miRNAs makes it difficult to design primers, these methods suffer from error-prone amplification, cross hybridization, and a lack of valid internal controls that hinder their sensitivity and specificity. These techniques involve highly complex assay protocols, chemical or enzymatic amplification, and expensive detection instruments that make them suitable only for laboratory-based usage at low throughput. Although various approaches have been applied toward miRNA detection, most approaches require chemical or enzymatic amplification of the target, and large expensive instruments. Thus, there is a need to provide techniques for detection of miRNAs that are more efficient, more reliable, less expensive, and suitable for more widespread application.

SUMMARY

In one aspect, example embodiments provide a method that can be used to detect at least a first analyte (e.g., a target miRNA sequence) in a sample. The method involves mixing the sample with an assay medium that comprises first nanoparticles that are functionalized to specifically bind to the first analyte to form first-analyte-bound nanoparticles. The method further involves selectively binding a number of the first-analyte-bound nanoparticles to a surface of a photonic crystal in a first capture spot, illuminating the surface of the photonic crystal with incident light, receiving reflected light that has reflected from each area in a first plurality of areas encompassing the first capture spot in response to illumination by the incident light, and determining, for each are in the first plurality of areas, a respective intensity value of a respective wavelength in the reflected light. The method additionally involves identifying one or more areas of the first plurality of areas having reduced intensity values, determining the number of the first-analyte-bound nanoparticles bound to the surface of the photonic crystal based on the identified one or more areas of the first plurality of areas, and correlating the number of the first-analyte-bound nanoparticles bound to the surface of the photonic crystal with an abundance of the first analyte in the sample.

In another aspect, example embodiments provide an apparatus that can be used to detect at least a first analyte (e.g., a target miRNA sequence) in a sample. The apparatus comprises a microfluidic system, a photonic crystal, a light source, a camera, and an analysis system. The microfluidic system is configured to receive a sample and an assay medium that comprises first nanoparticles. The first nanoparticles are functionalized to specifically bind to a first analyte to form first-analyte-bound nanoparticles, and a first capture spot on a surface of the photonic crystal is functionalized to specifically bind to the first-analyte-bound nanoparticles. The light source is configured to illuminate the surface of the photonic crystal with incident light. The camera is configured to receive reflected light that has reflected from each area in a first plurality of areas encompassing the first capture spot in response to illumination by the incident light. The analysis system is configured to determine, for each area in the first plurality of areas, a respective intensity value of a respective resonant wavelength in the reflected light, identify one or more areas of the first plurality of areas having reduced intensity values, determine a number of the first-analyte-bound nanoparticles bound to the surface of the photonic crystal based on the identified one or more areas of the first plurality of areas, and correlate the number of the first-anlayte-bound nanoparticles bound to the surface of the photonic crystal with an abundance of the first analyte in the sample.

DETAILED DESCRIPTION

1. Overview

Figure 1:
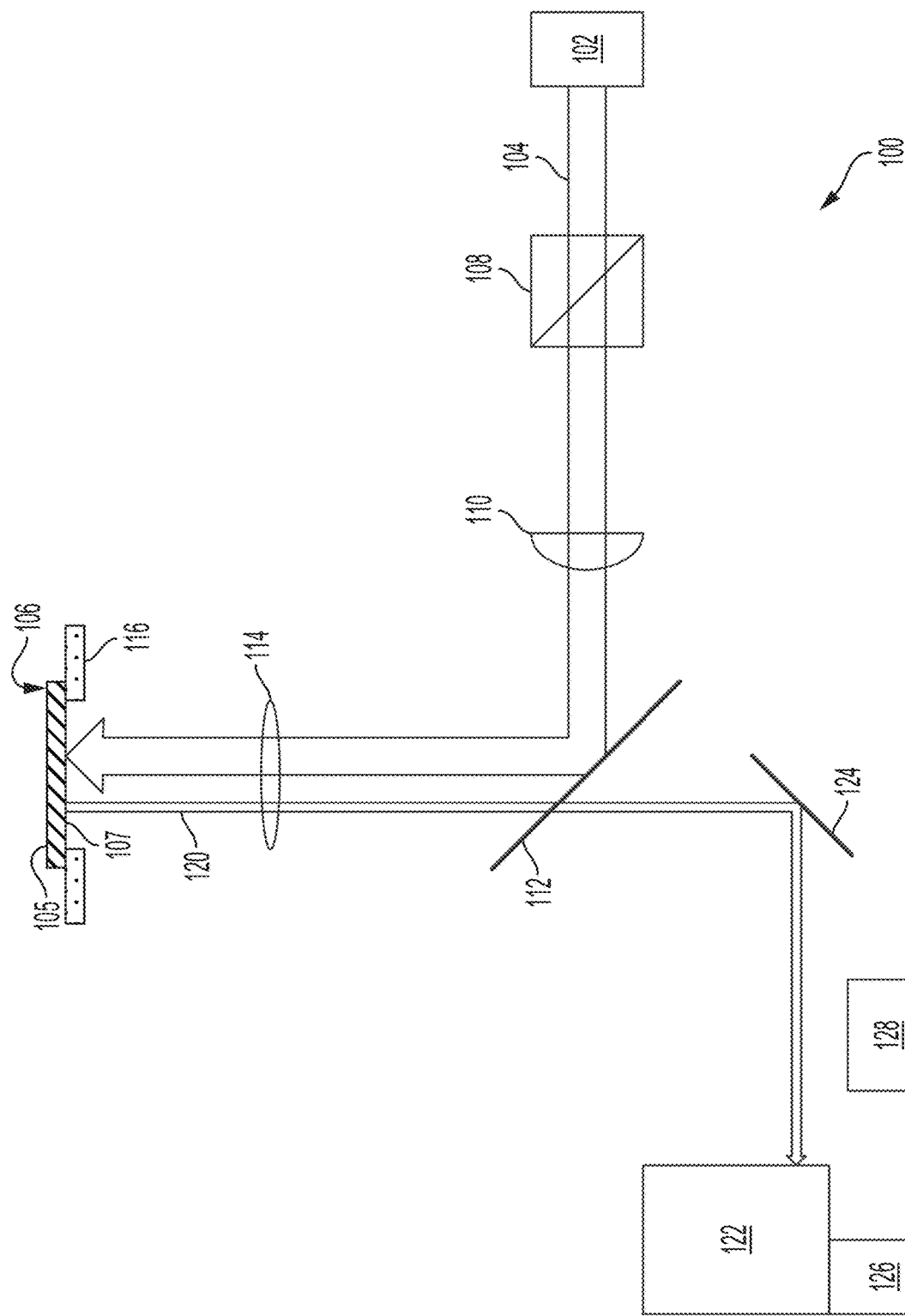
FIG. 1 is a schematic diagram of a photonic resonator absorption microscopy (PRAM) instrument, in accordance with an example embodiment.

Photonic crystal (PC) biosensors have been demonstrated as a highly versatile technology for a variety of label-free assays including high-throughput screening of small molecule-protein interactions, characterization of protein-protein interactions, and measurement of cell attachment modulation by drugs. A PC is a sub-wavelength grating structure consisting of a periodic arrangement of a low refractive index material coated with a high refractive index layer. When the PC is illuminated with a broadband light source, high order diffraction modes couple light into and out of the high index layer, destructively interfering with the zeroth-order transmitted light. At a particular resonant wavelength and incident angle, complete interference occurs and no light is transmitted, resulting in nearly 100% reflection efficiency. Various aspects of photonic crystal biosensors are described in U.S. Pat. Nos. 7,479,404, 7,521,769, 7,531,786, 7,737,392, 7,742,662, and 7,968,836, which patents are incorporated herein by reference.

When a material is adsorbed on the surface of a PC, the resonant reflection from the PC can be affected in two ways. First, the adsorbed material can cause a shift in the resonant Peak Wavelength Value (PWV), typically shifting the PWV to longer wavelengths. Second, the adsorbed material can cause a reduction in the Peak Intensity Value (PIV) at the resonant wavelength. Both of these effects, the shift in the PWV and the reduction in the PIV are highly localized. Thus, different locations on the surface of the PC may have different PWVs and different PIVs, depending on the materials at those locations.

Two mechanisms exist for locally reducing the reflected intensity from a PC at the resonant wavelength: absorption and scattering. The absorption mechanism is believed to work in the following manner. A substance that possesses optical absorption at the resonant wavelength of the PC will locally reduce the intensity of the resonant wavelength due to a mechanism through which the attached material (i.e., within the evanescent field region on the surface of the PC) gathers energy into itself, where it is dissipated by heating the surrounding environment. If the reflected intensity from the PC is observed at the PC resonant wavelength, one would observe a "hole" in the reflected intensity at the location of the optical absorber. Typical absorbing materials may include metals (e.g., Au, Ag, Pd), semiconductors, quantum dots, or colored polymers. Alternatively, a material attached to the PC surface that is not an optical absorber may cause a localized reduction in the intensity of the resonant wavelength if the material has sufficient dielectric permittivity contrast to its surrounding environment to outcouple light from the PC by scattering.

Previous work has demonstrated a label-free biosensor imaging approach that utilizes a PC to detect individual dielectric and metal nanoparticles though measurement of localized shifts in the resonant wavelength and localized reductions in the magnitude of the resonant reflection from the PC. See Y. Zhuo, H. Hu, W. L. Chen, M. Lu, L. M. Tian, H. J. Yu, K. D. Long, E. Chow, W. P. King, S. Singamaneni, B. T. Cunningham, "Single nanoparticle detection using photonic crystal enhanced microscopy," *Analyst*, vol. 139, pp. 1007-1015 (2014). It was found that metal nanoparticles having a strong absorption at the resonant wavelength attached to the PC surface induced a highly localized reduction in reflection efficiency. Using a microscopy-based approach, the resonant reflection properties of the PC surface could be scanned with a spatial resolution of about 0.6 μm.

Disclosed herein are methods and systems that make use of Photonic Resonator Absorption Microscopy (PRAM) in which individual particles (e.g., metal nanoparticles) on the surface of the PC are identified and counted based on local reductions in PIV caused by the particles' absorption at the resonant wavelength. The ability to count individual particles can be used to provide digital assays. For example, a metal nanoparticle can be functionalized to specifically bind to an analyte, such as a protein, a nucleic acid sequence, or other biomolecule, and the surface of the PC can be functionalized to specifically bind to functionalized nanoparticles that have bound to the analyte. The functionalized PC surface can then be exposed to a sample that includes the analyte and the functionalized nanoparticles and scanned for PIV. The locations of locally reduced PIV can be counted to determine how many analyte-bound nanoparticles have bound to the surface of the PC. This number can then be used to calculate an abundance of the analyte in the sample. This approach can be very useful for detecting biomolecules that are present in a sample in very low abundance, as individual biomolecules in the sample are counted by counting the metal nanoparticles to which they are bound. Applications include detection of disease biomarkers that comprise nucleic acids (e.g., micro RNA, messenger RNA, circulating tumor RNA), intact viruses (e.g., HIV, Dengue, Zika), or proteins (e.g., growth factors, cytokines, antibodies).

2. Example PRAM Instrument

Example embodiments make use of a PRAM instrument that uses a line-scanning approach to measure the spatial distribution of PWV and PIV across a PC surface with submicron spatial resolution for label-free imaging. A schematic diagram of an example PRAM instrument 100 is shown in FIG. 1. In this example, the PRAM instrument 100 includes an LED 102 as a light source. In one example, LED 102 is a Thorlabs M617F1 fiber-coupled LED, with a nominal wavelength of 617 nm and a bandwidth (FWHM) of 18 nm. Light 104 emitted from the LED 102 is directed to a PC 106 via a polarizing beam splitter (PBS) cube 108, cylindrical lens 110, beamsplitter 112, and objective lens 114. The PBS cube 108 linearly polarizes light 104 so that the electric field vector is oriented perpendicular to the grating structure when incident upon the PC. The cylindrical lens 110 focuses the light 102 to a line at the back focal plane of the objective lens 114 via the beamslitter 112. In representative examples, the cylindrical lens 110 has a focal length of 200 mm and the objective lens 114 is a 10× or 40× microscope objective.

The PC 106 has an upper surface 105 where the sample (not shown) is placed and a lower surface 107 opposite the upper surface 105. The PC 106 is illuminated from below at normal incidence (e.g., illuminated through the lower surface 107) by the light 104 passing through objective lens 114. The objective lens 114 focuses the light 102 to a focal line on the surface of the PC 106 such that the focal line is substantially perpendicular to the grating direction. To illuminate different portions of the PC 106, the lower surface 107 of PC 106 is supported on a motorized stage 116. The motorized stage 116 can move the PC 106 relative to the objective lens 114 so that different linear regions of the upper surface 105 can be illuminated by the focused light from the objective lens 114.

The reflected light 120 from the PC 106 contains the resonant reflected spectrum. The reflected light 120 passes through the objective lens 114 (in a direction opposite to that of light 104) and is directed to an entrance slit (30 μm wide) at the input of an imaging spectrometer 122 via beamsplitter 112 and mirror 124. The imaging spectrometer 122 is coupled to a CCD camera 126, which records the spectrum of the reflected light 120 as an image. Each image recorded by the CCD camera 126 includes the spectrum for each pixel across a line on the PC 106 that is illuminated by light 104. In one example, the spectrometer 122 is a grating-based spectrometer (300 lines/mm from Acton Research Corp.) and the CCD camera 126 has 512×512 pixels (Photometrics Cascade 512).

Using this method, reflected light is collected from a linear region of the PC 106, where the width of the imaged line (e.g., 1.2 μm) is determined by the width of the entrance slit of the imaging spectrometer and the magnification power of the objective lens. The line of reflected light, containing the resonant biosensor signal, is diffracted by the grating within the spectrometer to produce a spatially resolved spectrum for each point along the line. Each pixel across the line is converted to a resonant reflection spectrum containing a narrow bandwidth ($\Delta\lambda \sim 4$ nm) reflectance peak from the PC. The Peak Wavelength Value (PWV) and Peak Intensity Value (PIV) of each peak are determined by fitting the spectrum to a $2^{nd}$ order polynomial function, and then mathematically determining the maximum wavelength of the function. By fitting all 512 spectra, a line of 512 pixels is generated that represents one line of a PWV or PIV image of the sample on PC surface. With a 10× objective lens and an effective magnification of 26×, each pixel in the line represents a ~0.6 μm width on the PC surface and 512 such pixels cover a total width of ~300 μm (x dimension).

The PIV may be determined by multiple possible methods. For example, the intensity value assigned to a peak may be determined by simply reading the magnitude of the highest intensity wavelength in the reflected spectrum. Alternatively, the intensity of the reflected peak may be determined by integrating the reflected intensities over a range of wavelengths that comprise part or all of the reflected wavelengths. Further, the PIV value may be normalized by dividing the measured intensity of a peak by a reflected intensity of known value, such as the intensity reflected by a mirror, or by the intensity of a "clean" portion of the PC that is known to be free of surface-adsorbed biological material.

To generate a two-dimensional PIV image of the sample on the PC surface, the motorized stage 116 (Applied Scientific Instruments, MS2000) translates the PC 106 along the axis perpendicular to the imaged line (y dimension) in increments of 0.6 μm/step. Using this technique, a series of lines are assembled into an image at a rate of 0.1 sec/line and the same area on the PC surface can be scanned repeatedly. Each image is comprised of 512 by n pixels, where n can be selected during each scan session, and each pixel represents a 0.6×0.6 µm² region of the PC surface. The PRAM instrument and sensor structure measures the resonant reflection characteristics of the PC via the spectrum obtained from each 0.6×0.6 µm² pixel, representing about a 300×300 µm² region of the PC surface. High spatial resolution in the axial direction is obtained due to the shallow evanescent-field of the PC. Resolution in the lateral direction is determined by the lateral propagation distance of resonant-coupled photons, resulting in detection of distinct surface-attached objects for widely dispersed features at the 10-100 nm size scale.

The PIV image can be generated by an analysis system 128 coupled to the CCD camera 126. The analysis system 128 may also control the motorized stage 116. The analysis system 128 could be, for example, a computing device that is programmed with software for analyzing the images acquired by the CCD camera 126, to determine resonant wavelengths and intensities of resonant wavelengths and to generate PIV images (the analysis system 128 could also generate PWS images based on PWV shifts). The analysis system 128 could also be programmed to analyze PIV images for digital assays. Such analysis by the analysis system 128 could involve identifying areas in the PIV image that have reduced PIV and counting the number of particles bound to the surface of a PC based on the number of reduced-PIV areas in the PIV image. The analysis system 128 could also correlate the number of particles bond to the surface of the PC with an abundance of an analyte in the sample, for example, based on each bound particle being bound to one instance of the analyte. Thus, the analysis system 128 may include a processor and non-transitory data storage that stores instructions that are executable by the processor to perform any of the functions described herein.

Figure 2A:
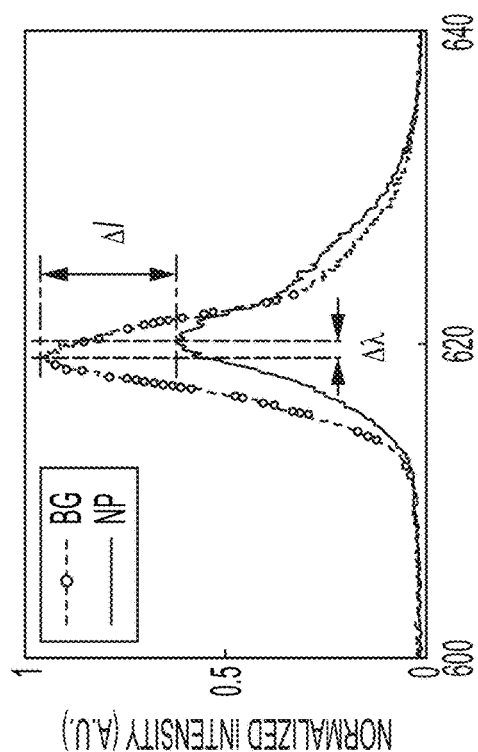
FIG. 2a illustrates representative reflection spectra from a bare photonic crystal surface (BG) and from a photonic crystal surface with a nanoparticle (NP) on the surface that strongly absorbs light at the resonant wavelength, in accordance with an example embodiment.
Figure 2C:
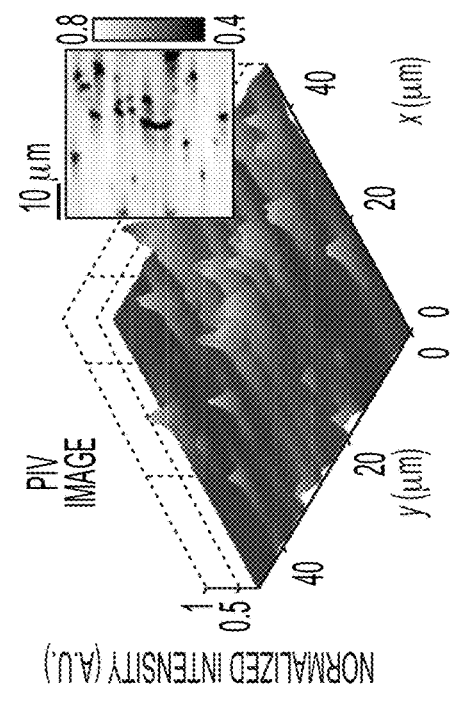
FIG. 2c shows a three-dimensional (3-d) image and a two-dimensional (2-d) image generated from peak intensity value (PIV) data in reflection spectra from a photonic crystal, in accordance with an example embodiment.
Figure 2B:
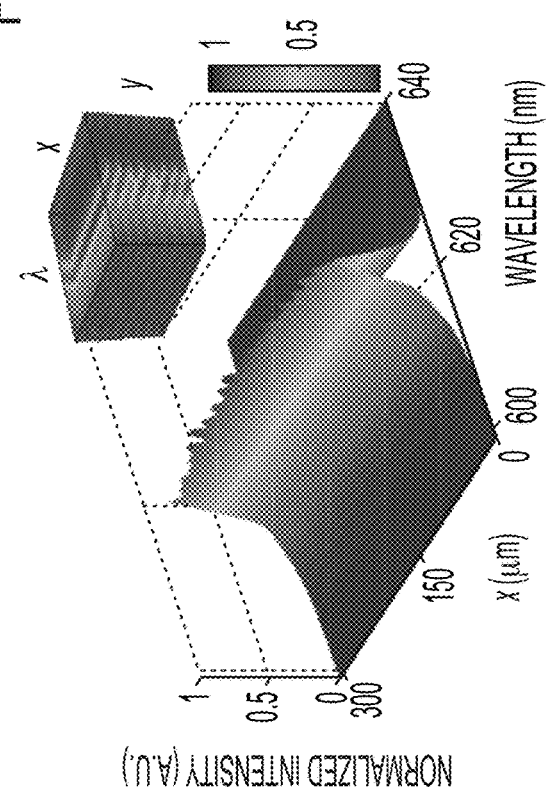
FIG. 2b illustrates representative reflection spectra from multiple areas of a photonic crystal surface, in accordance with an example embodiment.

FIG. 2a illustrates representative reflection spectra from a bare PC surface (BG) and from a PC surface with a nanoparticle (NP) on the surface that strongly absorbs light at the resonant wavelength. As shown, the presence of the nanoparticle shifts the PWV by an amount $\Delta\lambda$ and reduces the PIV by an amount $\Delta I$. FIG. 2b illustrates the spectra that may be obtained for a line (300 µm in the x direction) on the PC surface and further illustrates how multiple lines may be scanned in the y direction, for example, using the PRAM instrument described above. The data from the scans can be used to form a PIV image as shown in FIG. 2c. In the 3-d image shown in FIG. 2c, the "normalized intensity" axis indicates the amount of PIV reduction, so that the peaks in the 3-d image represent locations of maximal PIV reduction. In the 2-d inset image shown in FIG. 2c, locations of maximal PIV reduction are shown as dark spots. In these images, the locations of individual surface-absorbed nanoparticles can be identified based on the locations of maximal PIV reduction.

3. Example Assays

In one example, the PRAM instrument described above could be used with metal nanoparticles to detect miRNAs as biomarkers of cancer progression. In particular, the approach described below could be used to quantitatively measure the concentrations of multiple target biomolecules from a small blood sample (about 10 microliters) to monitor recurrence and response to therapy in cancer patients. Using this approach, the variation in target miRNA concentrations can be monitored on a routine and frequent basis during the course of therapy, so that the success or failure of a drug regimen may be assessed to enable more personalized patient care. The miRNAs that are detected in this way could be patient-specific or may identify a particular sub-class of cancer, thereby enabling a more personalized diagnosis and therapy.

A typical sample may include one or more target miRNA sequences (e.g., sequences that represent mutations of interest) in low abundance along with much higher concentrations of non-target miRNA sequences. For example, only about 400 to 500 copies of a target miRNA sequence may be present in a 10 µL of blood, which is equivalent to roughly 100 attomolar concentration, far below the threshold detection of common measurement technologies. To successfully detect the one or more target miRNA sequences in such a sample, the assay should provide both high sensitivity and high specificity. The ability to count individual nanoparticles on the surface of the PC and, thus, individual biomolecules (e.g., miRNAs) bound to the nanoparticles provides a digital assay with high sensitivity. While ultrasensitive assay technologies with capability for digital precision for observing the presence of a small number of analyte molecules in a test sample are becoming available, their complex assay protocols, high cost, and large size are less adaptable to frequent, noninvasive monitoring.

Figure 3:
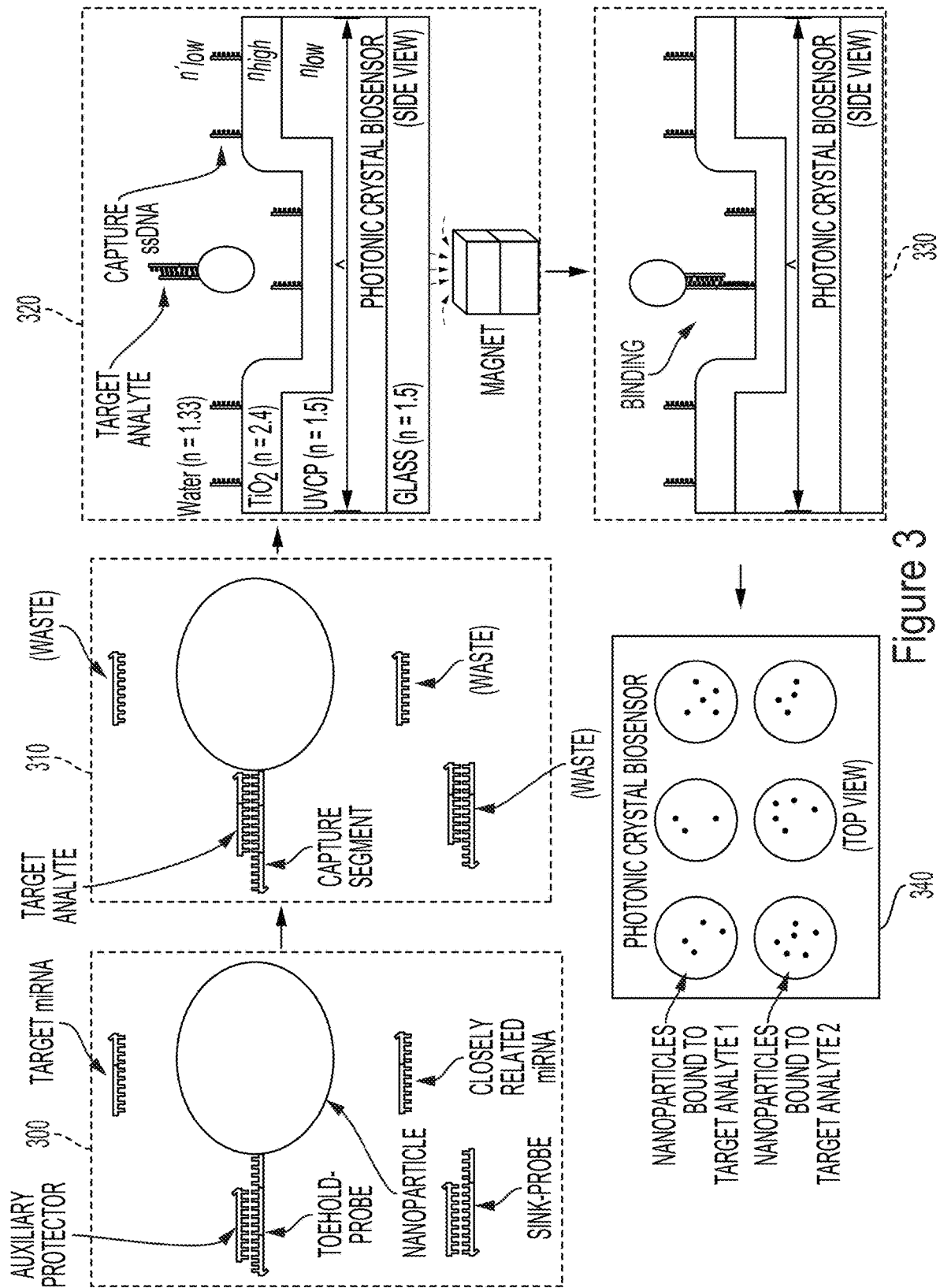
FIG. 3 schematically illustrates the use of toehold-probes in an assay for target miRNAs, in accordance with an example embodiment.

To achieve high specificity, the nanoparticles can be functionalized with "toehold-probes" (named for the shape of the probe molecule) and sink-probes that have large ratios (e.g., up to 500× ratios) in binding affinity between target sequences and closely related non-target sequences. FIG. 3 schematically illustrates the use of toehold-probes in an assay for target miRNAs. In this example, target analytes (miRNA sequences) in a sample are detected by mixing the sample with an assay medium that includes nanoparticles that have been functionalized with toehold-probes that specifically bind to a target miRNA. The nanoparticles that have bound to a target miRNA bind to the surface of a PC and can be counted by acquiring a PIV image of the surface of the PC (e.g., as shown in FIG. 2b). The abundance (e.g., concentration) of a target miRNA in the sample can then be determined based on the number of nanoparticles bound to the target miRNA.

Block 300 of FIG. 3 illustrates components of the assay medium after it has been mixed with the sample. As shown in block 300, the assay medium includes a nanoparticle that is functionalized with a toehold-probe that is hybridized with a shorter, auxiliary protector. In an example embodiment, the nanoparticles are gold-coated magnetic nanoparticles (~30×30×60 nm³). Also shown in block 300 are a target miRNA and a closely related non-target miRNA from the sample and a sink-probe that is provided in the assay medium. The target miRNA competes with the auxiliary protector for binding to the toehold-probe.

Block 310 illustrates the components in the mixture after the target miRNA (target analyte) has displaced the auxiliary probe from the toehold-probe. The auxiliary probe dissociates from the toehold-probe via stand displacement to become waste. The displacement of the auxiliary probe by the target miRNA reveals a capture segment of the toehold-probe. The capture segment is a ssDNA sequence that binds to a complementary ssDNA sequence printed on the surface of the PC biosensor, as illustrated in blocks 320 and 330. To achieve high specificity toward the target miRNA, the assay medium includes a sink probe that preferentially binds and inactivates a non-target miRNA, as shown in block 310. Thus, the sink-probe reduces the extent of binding from non-target miRNAs (and the sink-probe will not be attached to nanoparticles). When the sink-probe binds with its complementary partner, it can be removed by washing. The washing can occur while the magnetic nanoparticles are held by an external magnetic field.

After washing, the magnetic nanoparticles are drawn to the surface of the PC biosensor by a magnet (as shown in block 320), and the magnetic nanoparticles bind to the surface of the PC biosensor by the capture segments binding to their complementary ssDNA sequences (as shown in block 330). As illustrated in block 340, different capture spots on the PC surface can be printed with different ssDNA sequences that bind to nanoparticles that are functionalized to bind to different target miRNA sequences. Thus, nanoparticles bound to target analyte 1 may bind to the PC surface in a first capture spot, nanoparticles bound to target analyte 2 may bind to the PC surface in a second spot, etc., as shown in block 340. As shown, the PC surface has six capture spots. However, a greater or fewer number of capture spots could be provided on the PC surface. A PIV image of the PC surface (including the six capture spots) may be acquired and analyzed (e.g., using the PRAM instrument shown in FIG. 1). The analysis of the PIV image may involve counting the number of nanoparticles in each capture spot based on areas of reduced PIV. Thus, as shown in block 340, four nanoparticles bound to target analyte 1 may be counted in the first capture spot and six nanoparticles bound to target analyte 2 may be counted in the second capture spot. The number of bound nanoparticles in the first capture spot can then be correlated with an abundance of target analyte 1 in the sample and the number of bound nanoparticles in the second capture spot can be correlated with an abundance of target analyte 2 in the sample.

Figure 4C:
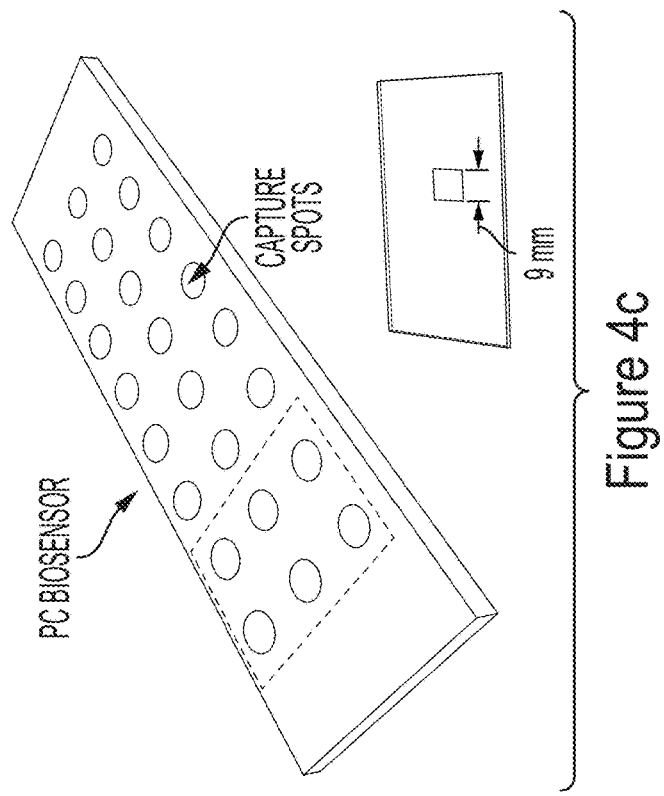
FIG. 4c is a view of photonic crystal biosensor with multiple capture spots, in accordance with an example embodiment.
Figure 4A:
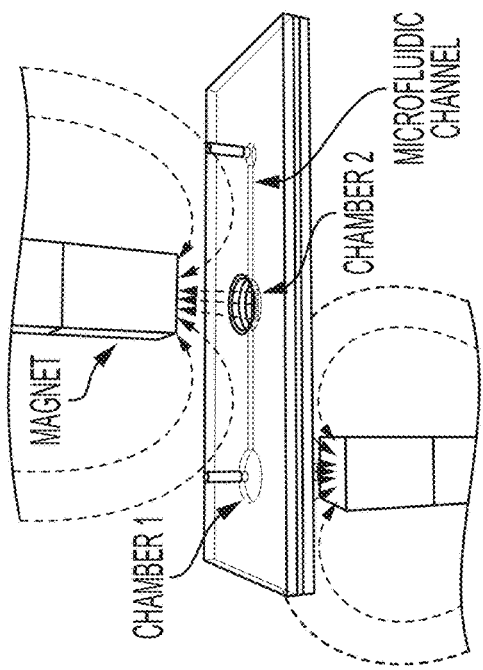
FIG. 4a is a view of a microfluidic system, in accordance with an example embodiment.
Figure 4B:
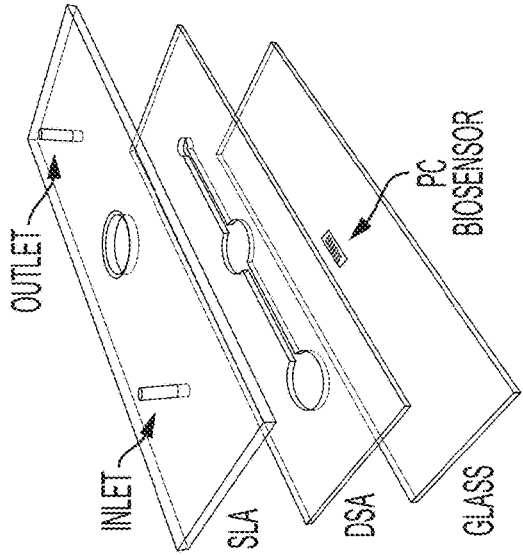
FIG. 4b is an exploded view of the microfluidic system of FIG. 4a, in accordance with an example embodiment.

To facilitate the assay steps illustrated in FIG. 3 and described above, a microfluidic system may be used. FIGS. 4a and 4b illustrate an example microfluidic system that includes two chambers (Chamber 1 and Chamber 2), in inlet to Chamber 1, a first microfluidic channel that connects Chamber 1 to Chamber 2, and a second microfluidic channel that connects Chamber 2 to an outlet. FIG. 4b illustrates a layered construction for the example microfluidic system. The bottom layer is a glass slide on which a PC biosensor is fabricated. The top layer is a stereolithographically-formed layer (SLA) that includes the inlet, the outlet, and an opening for Chamber 2. Between the top and bottom layers is a double-sided adhesive (DSA) layer that defines Chamber 1, the first microfluidic channel, Chamber 2, and the second microfluidic channel. The SLA layer is joined to the DSA layer such that the inlet in the SLA layer is positioned over Chamber 1 in the DSA layer, the Chamber 2 opening in the SLA layer is positioned over Chamber 2 in the DSA layer, and the outlet in the SLA layer is positioned over the end of the microfluidic channel in the DSA layer. The DSA layer is joined to the glass slide such that Chamber 2 is positioned over the PC biosensor. As shown in FIG. 4c, the PC biosensor has an array of capture spots used that are used to detect different miRNAs. Each capture spot is printed with a specific ssDNA that binds to the capture segment of a toehold-probe that binds to a specific miRNA.

In operation, a droplet of serum is mixed with an assay medium in Chamber 1. The assay medium includes gold-coated magnetic nanoparticles that are functionalized with toehold-probes as shown in FIG. 3 and described above. The target miRNAs bind to the toehold-probes, thereby exposing the capture segments. The assay medium also includes sink-probes that bind to non-target miRNAs in order to substantially reduce the likelihood that they will nonspecifically bind to the toehold-probes intended for the target miRNAs. The magnetization of the gold-coated magnetic nanoparticles enables them to be manipulated by a magnetic field. For example, magnetic manipulation can be used to mix the assay medium with the sample. After mixing, a magnet can then be used to move the magnetic nanoparticles from Chamber 1 through the first microfluidic channel to Chamber 2.

In Chamber 2, the nanoparticles that have bound to a particular target miRNA have exposed capture segments that bind to the complementary ssDNA sequence printed in the capture spot for that particular target miRNA on the PC biosensor. In this way, nanoparticles that have captured different miRNAs will accumulate in different areas on the PC biosensor. A PIV image of the PC surface can then be obtained using the PRAM instrument described above, and the number of nanoparticles in each capture spot can be counted in the PIV image. Typically, each nanoparticle represents one target miRNA. Thus, the assay provides for digital detection of each type of target miRNA.

It is to be understood that the digital detection of miRNAs is only one application of PRAM. The PRAM technique may be used to detect individual instances of other types of biomolecules (e.g., proteins, other nucleic acids, etc.) or individual instances of other types of particles, such as viruses. For example, the nanoparticles and the PC surface may be functionalized to bind to a specific type of virus. In this approach, a sample is mixed with an assay medium that includes the functionalized nanoparticles so that individual nanoparticles bind with individual viruses of that type present in the sample. The nanoparticles are then introduced to the functionalized PC surface so that the virus-bound nanoparticles are bound to the PC surface. The number of bound nanoparticles on the surface of the PC surface can be counted using PRAM. The number of bound nanoparticles can be correlated with the number of bound viruses (e.g., in a 1:1 ratio) and, thus, correlated with an abundance of that type of virus in the sample.

4. Example Nanoparticles

In example implementations, the nanoparticles used to obtain PRAM images (e.g., for digital assays) could have dimensions ranging from about 10 nm to about 500 nm. The nanoparticles could have a spherical shape, an ellipsoidal shape, or could be rod shaped. To achieve a PIV reduction with a high signal-to-noise ratio, the nanoparticles could include a metal or other material that strongly absorbs the resonant wavelength of the PC biosensor with which the nanoparticles are to be used. In the case of a metal, such as gold, silver, or palladium, the size, shape, and structure of the nanoparticle can be selected such that the metal has a surface plasmon resonance that matches the resonant wavelength of the PC biosensor. For example, core-shell and yolk-shell structures allow for control of the localized surface plasmon resonance (LSPR) wavelength from visible to near infrared wavelengths.

To allow for magnetic manipulation, the nanoparticles can also incorporate magnetic materials. The magnetic material in a nanoparticle could be a ferromagnetic material or any other material that enables the nanoparticle to be attracted to a magnet. To provide for both the desired optical and magnetic properties, the nanoparticles could have a multi-layer structure. For example, a nanoparticle could include a layer of a metal (e.g., gold) with a surface plasmon resonance that matches a PC biosensor resonant wavelength over a core of magnetic material (e.g., $Fe_3O_4$). Alternatively, the magnetic material may cover some or all of the metal in the nanoparticle, or the magnetic material may be interspersed throughout the nanoparticle.

5. Example PC Biosensor Structure

In an example embodiment, the PC biosensor is fabricated by a nanoreplica molding approach. Deep-UV lithography and reactive ion etching are used to produce a silicon wafer molding template with a negative image of the desired grating profile. A thin layer of liquid epoxy polymer (UV-curable) is deposited between the wafer template and glass substrate and then cured to solid phase by exposing it to a high intensity UV lamp. The nano-patterned surface in the epoxy polymer is transferred to the glass substrate after peeling off the wafer template. Finally, a thin $TiO_2$ film (about 80 nm thick) is sputtered over the grating structure using reactive RF sputtering. The resulting device has a linear grating surface structure (period=400 nm, depth=120 nm) that is integral to a conventional transparent glass cover slip, producing a resonant narrowband optical reflection at about 620 nm when the PC is covered in aqueous media (with a full-width-half maximum of about 4 nm).

6. Portable PRAM Instrument

Figure 5A:
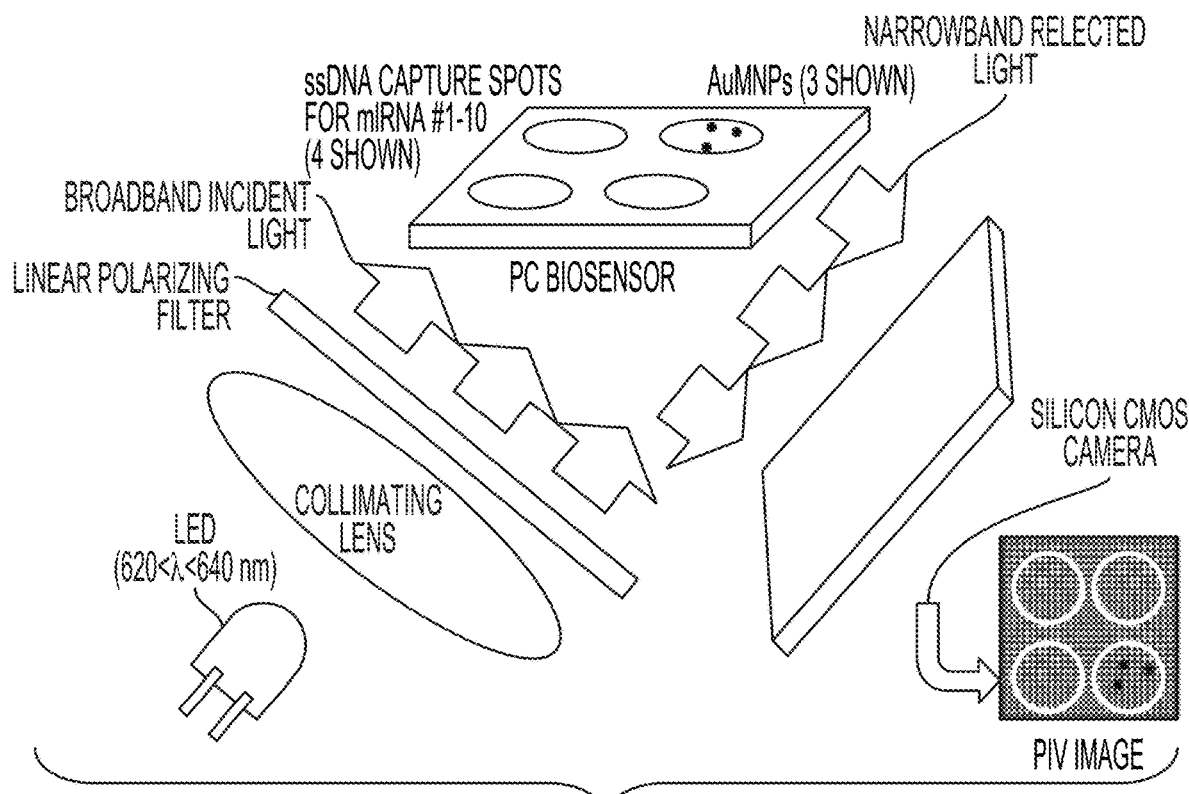
FIG. 5a is a schematic diagram of a portable PRAM instrument, in accordance with an example embodiment.

FIG. 5a is a schematic diagram of a portable PRAM instrument that can be used for digital assays of miRNAs (or other analytes) in a sample. The portable PRAM instrument includes a LED that illuminates a PC biosensor with broadband light (e.g., light with a range of wavelengths that includes about 620 nm to about 640 nm) at an illumination angle of about 5 degrees, after being collimated by a collimating lens and polarized by a linear polarizer. The broadband incident light from the LED should include the range of resonant wavelengths of the PC when exposed to the sample and assay medium. The PC biosensor includes multiple capture spots defined by areas of ssDNA on the surface of the PC. FIG. 5a shows the upper surface of the PC biosensor with capture spots to detect ten different target miRNAs in the sample (though only four capture spots are shown). The ssDNA in each capture spot can be selected to bind to a particular capture segment of a toehold-probe on a nanoparticle (e.g., a gold-coated magnetic nanoparticle) after binding by a specific miRNA sequence, for example, as illustrated in FIG. 3 and described above.

The PC reflects only a narrow band of the LED wavelengths with ~100% reflection efficiency into the pixels of an uncooled silicon CMOS imaging camera. The reflected intensity is locally reduced by the adsorption of nanoparticles that have selectively adsorbed to their respective capture spots of ssDNA due to binding to a particular miRNA sequence. For example, FIG. 5a shows three nanoparticles (AuMNPs) in a particular capture spot on the PC biosensor, and also shows a PIV Image in which these three nanoparticles can be identified as dark spots. The PIV image (and analysis of the PIV image) can be generated by an analysis system (e.g., similar to analysis system 128 shown in FIG. 1) that is coupled to the CMOS imaging camera. In this way, the three nanoparticles shown in the capture spot can be detected individually in the resulting PIV image by the locations of reduced PIV and can be correlated to the presence of three copies the particular miRNA sequence that corresponds to that particular capture spot.

Figure 5B:
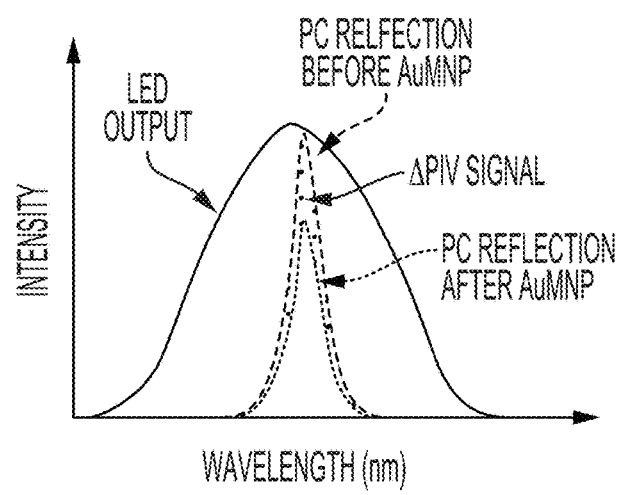
FIG. 5b illustrates a representative spectrum of incident light from the LED shown in FIG. 5a and representative spectra of light reflected from the PC biosensor shown in FIG. 5a before and after nanoparticles are bound to the surface of the PC biosensor.

The portable PRAM instrument shown in FIG. 5a differs from the PRAM instrument shown in FIG. 1 in that the CMOS imaging camera acquires an image of the PC biosensor (e.g., so as to include each of the capture spots) without a line-scanning approach and without a spectrometer. Thus, the CMOS camera obtains an image in which the brightness of each pixel represents the intensity of the reflected light from a particular area of the PC integrated over all of the reflected wavelengths. Nonetheless, because the reflected light is primarily at the resonant wavelength, the intensity of the reflected light represented by a pixel can be correlated with the intensity at the resonant wavelength. This is illustrated by the representative spectra shown in FIG. 5b. As shown, the reflected light from the PC includes a much narrower range of wavelengths than the incident light from the LED. The intensity of the reflected light is reduced by an amount (the ΔPIV Signal) when a nanoparticle (AuMNP) is on the surface of the PC. The ΔPIV Signal is shown as the difference in the integrated intensity of the reflected light.

It can be beneficial to establish an initial reflected intensity baseline and to subsequently identify pixels in which a ~2% intensity reduction occurs by kinetically gathering camera images at a 60 Hz frame rate. Using preliminary data for detection of gold nanoparticles, a 100 mW, λ=620 nm LED with its illumination spread over a 0.5×0.5 $cm^2$ PC surface area may reflect photons over the PC's ~2 nm resonant bandwidth, resulting in ~20,000 Photons/pixel for a 10 msec integration time. A reduced reflection intensity caused by adsorption of one nanoparticle may reduce the PC reflected intensity by ~2%, corresponding to a reflected intensity decrease of about 400 photons/pixel. Using a typical uncooled CMOS imaging chip (Hamamatsu C11440-10CORCA Flash2.8), the signal-to-noise ratio will be ~100 at the predicted intensity level, with a single-frame background noise of ~200 photons/pixel. However, with the ability to average the pixel values of N successive image captures, the signal-to-noise ratio may be increased by a factor of $N^{1/2}$, so for N=10, a total 100 msec data collection window can achieve an effective photon background noise of 63 photons/pixel. Thus, small intensity reductions caused by dynamic AuMNP capture are expected to be measurable with a signal-to-noise ratio that is 6 or greater.

In one approach, the PIV reduction can be computed as the difference between before and after nanoparticle binding images. Alternatively, ratiometric approaches for extracting local pixel intensity differences that involve modeling of the noise characteristics, adaptive thresholding and wavelet transforms could be used.

This portable PRAM instrument can be constructed from inexpensive, commercially available optical components and assembled into a compact desktop system. The system can further include a plastic 3-D printed enclosure for holding the components and alignment of the PC within a microfluidic cartridge (as shown in FIGS. 4a and 4b), and also a manual slider for the two magnets shown in FIG. 4a. A software interface can be provided to automate operation of the LED and CMOS camera, acquire PIV images during the assay, and analyze the images to count the pixels with reduced reflection intensity that correspond to nanoparticles in each capture spot.

7. Conclusion

PRAM is a new form of microscopy in which changes in resonant reflection efficiency from a PC surface are measured on a pixel-by-pixel basis to form a PIV image. Locations within the PIV image that undergo the largest reductions in resonant reflection efficiency represent locations in which an optical absorber (e.g., a metal nanoparticle) is present on the PC surface. Thus, the number of optical absorbers present in the PIV image can be counted. Such optical absorbers can be functionalized to specifically bind to a miRNA or other target analyte, and the PC surface can be functionalized to specifically bind to optical absorbers that have bound to the target analyte. The number of bound optical absorbers detected in the PIV image can be related to the number of individual instances of the target analyte in a ratio that is close to 1:1. In this way, PRAM can be used for digital assays of miRNAs or other target analytes. Further, an inexpensive, portable PRAM instrument can enable analyte detection with single molecule resolution in point-of-care settings.

What is claimed is:

1. An apparatus, comprising:
    a fluidic structure configured to receive a sample and an assay medium, wherein the assay medium comprises first nanoparticles, and wherein the first nanoparticles are functionalized to specifically bind to a first analyte in the sample to form first-analyte-bound nanoparticles;
    a photonic crystal within the fluidic structure, wherein a first capture spot on a surface of the photonic crystal is functionalized to specifically bind to the first-analyte-bound nanoparticles, wherein the first nanoparticles comprise a metal and have a surface plasmon resonance at a wavelength that matches a resonant wavelength of the photonic crystal;
    a light source outside of the fluidic structure, wherein the light source is configured to illuminate the surface of the photonic crystal with incident light;
    a camera outside of the fluidic structure, wherein the camera is configured to receive reflected light that has reflected from each area in a first plurality of areas encompassing the first capture spot in response to illumination by the incident light; and
    an analysis system outside of the fluidic structure, wherein the analysis system is configured to:
        determine, for each area in the first plurality of areas, a respective intensity value of a respective resonant wavelength in the reflected light;
        identify one or more areas of the first plurality of areas having reduced intensity values relative to an intensity value measured before binding the first-analyte-bound nanoparticles;
        determine a number of the first-analyte-bound nanoparticles bound to the surface of the photonic crystal based on the identified one or more areas of the first plurality of areas; and
        correlate the number of the first-analyte-bound nanoparticles bound to the surface of the photonic crystal with an abundance of the first analyte in the sample.

2. The apparatus of claim 1, wherein the fluidic structure comprises a first chamber for receiving the sample and the assay medium, and a second chamber fluidly coupled to the first chamber via a microfluidic channel, wherein the photonic crystal is disposed in the second chamber.

3. The apparatus of claim 2, wherein the first nanoparticles are magnetic, further comprising a magnet outside of the fluidic structure, wherein the magnet is configured to move the first nanoparticles from the first chamber to the second chamber via the microfluidic channel.

4. The apparatus of claim 1, wherein the assay medium further comprises second nanoparticles, wherein the second nanoparticles are functionalized to specifically bind to a second analyte in the sample to form second-analyte-bound nanoparticles, wherein a second capture spot on the surface of the photonic crystal is functionalized to specifically bind to the second-analyte-bound nanoparticles, and wherein the camera is further configured to receive reflected light that has reflected from each area in a second plurality of areas encompassing the second capture spot in response to illumination by the incident light.

5. The apparatus of claim 4, wherein the analysis system is further configured to:
    determine, for each area in the second plurality of areas, a respective intensity value of a respective resonant wavelength in the reflected light;
    identify one or more areas of the second plurality of areas having reduced intensity values relative to an intensity value measured before binding the second-analyte-bound nanoparticles;
    determine a number of the second-analyte-bound nanoparticles bound to the surface of the photonic crystal based on the identified one or more areas of the second plurality of areas; and
    correlate the number of the second-analyte-bound nanoparticles bound to the surface of the photonic crystal with an abundance of the second analyte in the sample.

6. The apparatus of claim 5, wherein the camera is configured to acquire an image of the surface of the photonic crystal from the reflected light, wherein a first plurality of pixels in the image encompasses the first capture spot and a second plurality of pixels in the image encompasses the second capture spot, and wherein brightness values of pixels in the first plurality of pixels are indicative of intensity values of resonant wavelengths in the reflected light from the first capture spot and brightness values of pixels in the second plurality of pixels are indicative of intensity values of resonant wavelengths in the reflected light from the second capture spot.

7. The apparatus of claim 4, wherein the first analyte is a first microRNA (miRNA) sequence and the second analyte is a second miRNA sequence.

8. The apparatus of claim 7, wherein the first nanoparticles are functionalized with a first toehold-probe that hybridizes with the first miRNA sequence and the second nanoparticles are functionalized with a second toehold-probe that hybridizes with the second miRNA sequence.

9. The apparatus of claim 8, wherein the assay medium further comprises one or more sink-probes, wherein the one or more sink-probes hybridize with one or more miRNA sequences that differ from the first and second miRNA sequences.

10. The apparatus of claim 1, wherein the metal is gold, silver, or palladium.

11. The apparatus of claim 1, wherein the first nanoparticles absorb light at wavelengths that include resonant wavelengths of the photonic crystal.

12. The apparatus of claim 1, wherein the light source comprises a light emitting diode (LED), wherein the LED emits light with a range of wavelengths that includes resonant wavelengths of the photonic crystal.

13. The apparatus of claim 1, further comprising a lens located between the light source and the photonic crystal, wherein the lens is configured to collimate the incident light.

14. The apparatus of claim 1, further comprising a polarizer located between the light source and the photonic crystal, wherein the polarizer is configured to polarize the incident light.

15. The apparatus of claim 1, wherein the photonic crystal comprises a grating structure formed by a periodic arrangement of a low refractive index material coated with a high refractive index material.

16. The apparatus of claim 15, wherein the incident light is polarized such that the incident light has an electric field vector oriented perpendicular to the grating structure of the photonic crystal.

17. The apparatus of claim 15, further comprising:
    an objective lens located between the light source and the photonic crystal; and a cylindrical lens located between the light source and the photonic crystal, wherein the cylindrical lens is configured to focus light emitted by the light source to a line at a back focal plane of the objective lens, and wherein the objective lens is configured to focus the light focused by the cylindrical lens to a focal line on the surface of the photonic crystal.

18. The apparatus of claim 17, wherein the focal line is substantially perpendicular to the grating structure of the photonic crystal.

19. The apparatus of claim 1, wherein the first nanoparticles are magnetic, further comprising a magnet outside of the fluidic structure, wherein the magnet is configured to draw the first nanoparticles to the surface of the photonic crystal.

* * * * *